(12) United States Patent
Zhao et al.

(10) Patent No.: US 12,271,524 B2
(45) Date of Patent: Apr. 8, 2025

(54) BRAIN-COMPUTER AIDED ANALYSIS METHOD AND SYSTEM FOR AVIATION ACCIDENT

(71) Applicant: Nanjing University of Aeronautics and Astronautics, Jiangsu (CN)

(72) Inventors: Qijun Zhao, Jiangsu (CN); Xu Zhou, Jiangsu (CN); Binwu Ren, Jiangsu (CN); Xiayang Zhang, Jiangsu (CN); Daoqiang Zhang, Jiangsu (CN); Bo Wang, Jiangsu (CN)

(73) Assignee: Nanjing University of Aeronautics and Astronautics, Nanjing (CN)

( * ) Notice: Subject to any disclaimer, the term of this patent is extended or adjusted under 35 U.S.C. 154(b) by 790 days.

(21) Appl. No.: 17/546,827

(22) Filed: Dec. 9, 2021

(65) Prior Publication Data
US 2022/0187914 A1 Jun. 16, 2022

(30) Foreign Application Priority Data
Dec. 10, 2020 (CN) .......................... 202011452178.1

(51) Int. Cl.
G06F 3/01 (2006.01)
A61B 5/00 (2006.01)
A61B 5/18 (2006.01)

(52) U.S. Cl.
CPC ................ *G06F 3/015* (2013.01); *A61B 5/18* (2013.01); *A61B 5/6887* (2013.01);
(Continued)

(58) Field of Classification Search
CPC ......... G06F 3/015; A61B 5/18; A61B 5/6887; A61B 5/7203; A61B 5/725; A61B 5/7267; A61B 2503/22
(Continued)

(56) References Cited

U.S. PATENT DOCUMENTS

2005/0099279 A1 5/2005 Forbes et al.
2009/0040054 A1 2/2009 Wang et al.
(Continued)

FOREIGN PATENT DOCUMENTS

CN 105361863 A 3/2016
CN 107516452 A 12/2017
(Continued)

OTHER PUBLICATIONS

Hongbing et al "On Methods of Human Factor Research in Civil Aviation" Journal of Civil Aviation Flight University of China vol. 26, pp. 5-10, 2015.

(Continued)

*Primary Examiner* — Naomi J Small
(74) *Attorney, Agent, or Firm* — Morse, Barnes-Brown & Pendleton, P.C.; Martin Z. Zhang (57) ABSTRACT

A brain-computer aided analysis method for an aviation accident is provided. The method includes the steps of obtaining historical electroencephalogram (EEG) signals and historical psychological and physiological features of various pilots during flight to be recorded as first EEG signals and first features; training a feature recognition model by using the first EEG signals as an input and the first features as an output; inputting EEG signals of a pilot of an aviation accident aircraft into the feature recognition model, and outputting psychological and physiological features of the pilot of the aviation accident aircraft to be recorded as second features; determining whether the second features are abnormal or not according to the historical psychological and physiological features of the pilot of the aviation accident aircraft and the first features.

10 Claims, 4 Drawing Sheets

(52) U.S. Cl.
CPC ............ *A61B 5/7203* (2013.01); *A61B 5/725* (2013.01); *A61B 5/7267* (2013.01); *A61B 2503/22* (2013.01)

(58) Field of Classification Search
USPC ......................................................... 340/576
See application file for complete search history.

(56) References Cited

U.S. PATENT DOCUMENTS

| | | | | |
|---|---|---|---|---|
| 2010/0076273 | A1* | 3/2010 | Shigetou | A61B 5/18 600/300 |
| 2012/0078063 | A1 | 3/2012 | Moore-Ede | |
| 2012/0289869 | A1* | 11/2012 | Tyler | A61N 7/00 601/2 |
| 2017/0312517 | A1* | 11/2017 | Phillips | G09B 9/08 |
| 2018/0032891 | A1* | 2/2018 | Ba | B60W 50/14 |
| 2020/0241525 | A1* | 7/2020 | Harbour | G06F 3/014 |

FOREIGN PATENT DOCUMENTS

| | | |
|---|---|---|
| CN | 107644566 A | 1/2018 |
| CN | 108133639 A | 6/2018 |
| CN | 108241431 A | 7/2018 |
| CN | 108523907 A | 9/2018 |
| CN | 110155349 A | 8/2019 |
| CN | 110367975 A | 10/2019 |
| CN | 111028611 A | 4/2020 |
| CN | 111680391 A | 9/2020 |
| CN | 111767611 A | 10/2020 |
| KR | 2018/0134310 A | 12/2018 |
| KR | 2019/0084679 A | 7/2019 |

OTHER PUBLICATIONS

Martensson et al "Driver Sleepiness Classification Based on Physiological Data and Driving Performance From Real Road Driving" Transactions on Intelligent Transportation Systems vol. 20, pp. 421-430, 2019.

Palaiahnakote et al "Pattern Recognition" 5$^{th}$ Asian Conference Revised Selected Papers Part II, 2019.

Wang et al."Brain Encephalofluctuograph Technology Monitoring and Analysis of 134 High Performance Fighter Pilots" Military Medical Journals China vol. 31, pp. 834-836, 2017.

Wei "Research on Human Errors and Workload Evaluation Method" Nanjing University of Aeronautics and Astronautics, 2014.

* cited by examiner

BRAIN-COMPUTER AIDED ANALYSIS METHOD AND SYSTEM FOR AVIATION ACCIDENT

CROSS REFERENCE TO RELATED APPLICATION

This patent application claims the benefit and priority of Chinese Patent Application No. 202011452178.1 filed on Dec. 10, 2020, the disclosure of which is incorporated by reference herein in its entirety as part of the present application.

TECHNICAL FIELD

The present disclosure relates to the technical field of accident analysis, and in particular, to a brain-computer aided analysis method and system for an aviation accident.

BACKGROUND ART

An aircraft generally uses a black box for information storage, i.e., an electronic flight recorder for recording flight and performance parameters of the aircraft. Information of the flight recorder may be used for flight accident analysis. Data and voice records recorded before the air crash are processed and sent into a flight simulator to reproduce the accident process and analyze the cause of the accident. The black boxes are divided into: cockpit voice recorder and flight data recorder. The former records conversations between pilots from takeoff to landing, and the latter records various data during the flight.

In order to obtain objective and comprehensive information during accident investigations, an amount of data such as flight data, audio data and video data, recorded by the black boxes are increasing, from a few to hundreds or thousands. Flight data generally includes aircraft and engine operating status, pilot control conditions, aircraft external information, etc. Audio data generally includes the conversation between the captain and copilot, the conversation between the plane and the ground, the conversation between the crew and the cockpit environment sound, etc. Video data generally includes cockpit instrument display, pilot action, the front view of the aircraft, landing gear retraction status, etc. When an accident occurs, through special data playback software, the black box data can be used to intuitively and truly reproduce the flight process of the aircraft and automatically analyze the potential faults of the aircraft and the abnormal operation of personnel. This helps to prevent the occurrence of any possible faults or accidents, greatly improving the level of aviation flight safety.

Each accident will bring about corresponding technological innovation, but there are few breakthroughs in accidents caused by human factors. The existing black box can only record in-cabin voice recording data and flight parameters, and cannot reflect the physiological and psychological status of the pilot during the flight, so subjective reasons from the pilot cannot be ruled out. In addition to investigating the background and recent life of the pilot after the accident, it is difficult to provide technical evidence that the accident is caused by human factors. The black box may record the status parameters of the aircraft during the flight and the call records during the flight, which may be used to reproduce the process after an accident. However, psychological factors of pilots and even terrorist incidents such as hijacking are also possible causes of accidents.

SUMMARY

An objective of the embodiments is to provide a brain-computer aided analysis method and system for an aviation accident. Aided analysis is performed in combination with electroencephalogram (EEG) signals of a pilot, such that causes of the aviation accident can be analyzed more comprehensively and objectively.

To implement the above objectives, the present disclosure provides the following solutions.

A brain-computer aided analysis method for an aviation accident includes:
  obtaining historical EEG signals and historical psychological and physiological features of various pilots during flight to be recorded as first EEG signals and first features;
  training a feature recognition model by using the first EEG signals as an input and the first features as an output;
  inputting EEG signals of a pilot of an aviation accident aircraft into the feature recognition model, and outputting psychological and physiological features of the pilot of the aviation accident aircraft to be recorded as second features;
  determining whether the second features are abnormal or not according to the historical psychological and physiological features of the pilot of the aviation accident aircraft and the first features; and
  if the second features is determined to be abnormal, analyzing causes of the aviation accident for the pilot of the aviation accident aircraft; or
  if the second features is determined to be not abnormal, performing accident simulation reproduction according to the second features to obtain reproduced accident information; and
  analyzing the causes of the aviation accident according to the reproduced accident information.

Optionally, obtaining the first EEG signals may specifically includes:
  obtaining the EEG signals of the various pilots during training flight in different flight environments to be recorded as second EEG signals;
  obtaining the EEG signals of the various pilots during actual flight in different flight environments to be recorded as third EEG signals; and
  correcting the second EEG signals by using the third EEG signals to obtain corrected EEG signals to be recorded as fourth EEG signals.

The first EEG signals may include the third EEG signals and the fourth EEG signals.

Optionally, the second EEG signals and the third EEG signals are obtained by a non-invasive method.

Optionally, the brain-computer aided analysis method for the aviation accident may further includes:
  performing signal denoising, artifact removal and feature extraction processing on the first EEG signals.

Optionally, the performing signal denoising, artifact removal and feature extraction processing on the first EEG signals may specifically includes:
  using an Faraday cage, a threshold method or a band-pass filter for signal denoising;
  using a linear model analysis method, a principal component analysis method or an independent component analysis method for artifact removal; and
  using a frequency domain analysis method or a time domain analysis method for feature extraction.

A brain-computer aided analysis system for an aviation accident includes:

an obtaining module, configured to obtain historical EEG signals and historical psychological and physiological features of various pilots during flight to be recorded as first EEG signals and first features;

a training module, configured to train a feature recognition model by using the first EEG signals as an input and the first features as an output;

a recognition module, configured to input EEG signals of a pilot of an aviation accident aircraft into the feature recognition model, and output psychological and physiological features of the pilot of the aviation accident aircraft to be recorded as second features;

a determining module, configured to determine whether the second features are abnormal or not according to the historical psychological and physiological features of the pilot of the aviation accident aircraft and the first features;

a first analysis module, configured to analyze causes of the aviation accident for the pilot of the aviation accident aircraft if the second features are abnormal;

a simulation reproduction module, configured to perform accident simulation reproduction according to the second features to obtain reproduced accident information if the second features are not abnormal; and a second analysis module, configured to analyze the causes of the aviation accident according to the reproduced accident information.

Optionally, the obtaining module may specifically includes:

a first obtaining unit, configured to obtain the EEG signals of the various pilots during training flight in different flight environments to be recorded as second EEG signals;

a second obtaining unit, configured to obtain the EEG signals of the various pilots during actual flight in different flight environments to be recorded as third EEG signals; and a correction unit, configured to correct the second EEG signals by using the third EEG signals to obtain corrected EEG signals to be recorded as fourth EEG signals.

The first EEG signals may include the third EEG signals and the fourth EEG signals.

Optionally, the second EEG signals and the third EEG signals are obtained by a non-invasive method.

Optionally, the brain-computer aided analysis system for the aviation accident may further includes:

a processing module, configured to perform signal denoising, artifact removal and feature extraction processing on the first EEG signals.

Optionally, the processing module may specifically includes:

a signal denoising unit, configured to use an Faraday cage, a threshold method or a band-pass filter for signal denoising;

an artifact removal unit, configured to use a linear model analysis method, a principal component analysis method or an independent component analysis method for artifact removal; and a feature extraction unit, configured to use a frequency domain analysis method or a time domain analysis method for feature extraction.

Based on specific embodiments provided in the present disclosure, the present disclosure has the following technical effects:

The present disclosure provides a brain-computer aided analysis method for an aviation accident. The method includes steps of obtaining historical EEG signals and historical psychological and physiological features of various pilots during flight to be recorded as first EEG signals and first features; training a feature recognition model by taking the first EEG signals as an input and the first features as an output; inputting EEG signals of a pilot of an aviation accident aircraft into the feature recognition model, and outputting psychological and physiological features of the pilot of the aviation accident aircraft to be recorded as second features; determining whether the second features are abnormal or not according to the historical psychological and physiological features of the pilot of the aviation accident aircraft and the first features; and if yes, analyzing causes of the aviation accident for the pilot of the aviation accident aircraft; or if not, performing accident simulation reproduction according to the second features to obtain reproduced accident information; and analyzing the causes of the aviation accident according to the reproduced accident information. According to the method, aided analysis is performed in combination with the EEG signals of the pilot, such that the causes of the aviation accident can be analyzed more comprehensively and objectively.

BRIEF DESCRIPTION OF THE DRAWINGS

To describe the technical solutions in the embodiments of the present disclosure or in the prior art more clearly, the accompanying drawings required for the embodiments will be briefly described below. Apparently, the accompanying drawings described below are merely some embodiments of the present disclosure, and a person of ordinary skill in the art may also obtain other accompanying drawings based on these accompanying drawings without creative efforts.

DETAILED DESCRIPTION OF THE EMBODIMENTS

The technical solutions of the embodiments of the present disclosure are clearly and completely described below with reference to the accompanying drawings. Apparently, the described embodiments are merely a part rather than all of the embodiments of the present disclosure. All other embodiments obtained by a person of ordinary skill in the art based on the embodiments of the present disclosure without creative efforts shall fall within the protection scope of the present disclosure.

Neuroscience research shows that after the brain produces the consciousness of action and before the action is executed, or after the subject is exposed to an external stimulus, the electrical activity of the nervous system will change correspondingly. Such changes in the electrical activity of the nervous system may be detected by certain means and serve as a characteristic signal that the action is about to happen. The present disclosure combines the brain-computer interface device to acquire the EEG signals of pilots during flight and synchronously store the EEG signals in the black box. Different from the previous records for external environment, the present disclosure increases the acquisition of psychological and physiological information from the individual EEG signals of the pilot and introduces the subjective possibility in aviation accident analysis. After an accident, the EEG signals of the pilot may be used to reproduce the psychological activities, thus assisting in the reproduction of external flight environment.

The objective of the present disclosure is to provide a brain-computer aided analysis method and system for an aviation accident. Aided analysis is performed in combination with the EEG signals of the pilot, such that the causes of the aviation accident can be analyzed more comprehensively and objectively.

To make the above-mentioned objectives, features, and advantages of the present disclosure clearer and more comprehensible, the present disclosure will be further described in detail below with reference to the accompanying drawings and the specific implementation.

Embodiment 1

Figure 1:
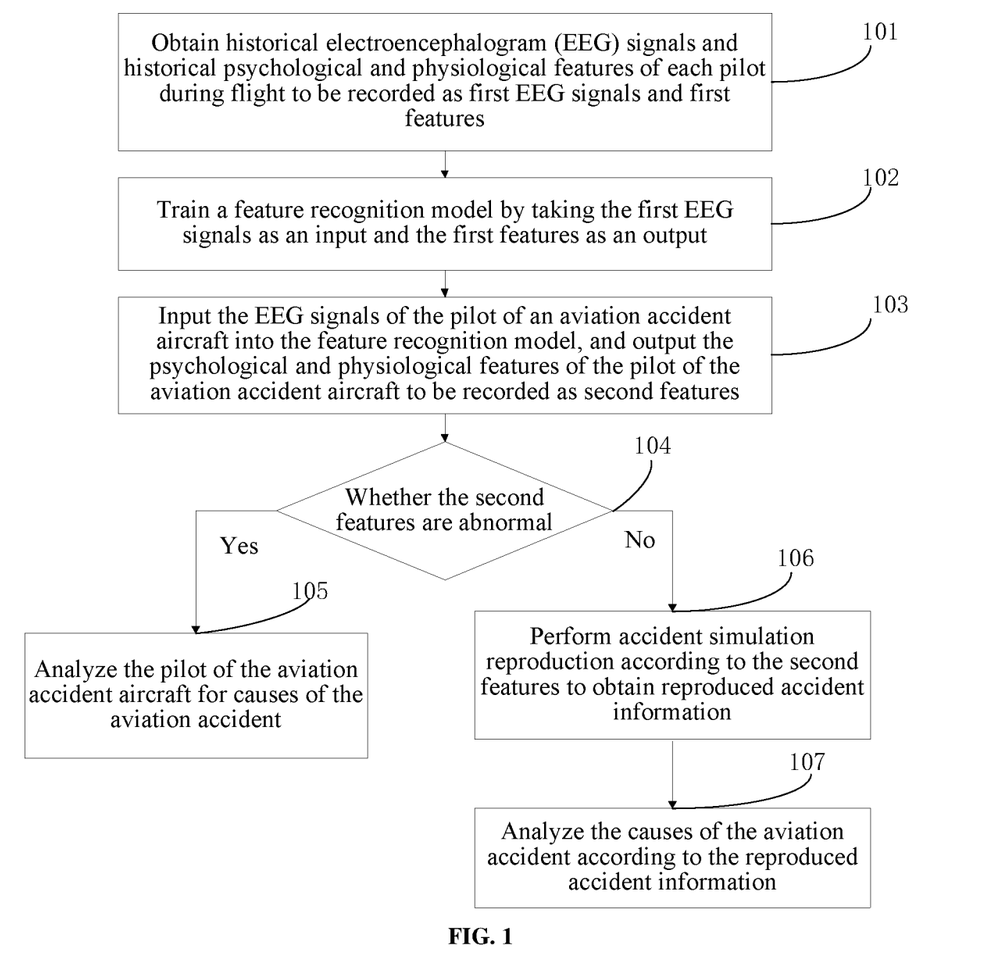
FIG. 1 is a flowchart of a brain-computer aided analysis method for an aviation accident according to Embodiment 1 of the present disclosure.

FIG. 1 is a flowchart of a brain-computer aided analysis method for an aviation accident according to Embodiment 1 of the present disclosure. As shown in FIG. 1, the brain-computer aided analysis method for the aviation accident includes the following steps 101 to 107.

In step 101, historical EEG signals and historical psychological and physiological features of various pilots during flight are obtained to be recorded as first EEG signals and first features.

In step 102, a feature recognition model is trained by taking the first EEG signals as an input and the first features as an output.

In step 103, the EEG signals of the pilot of an aircraft subject to an aviation accident are input into the feature recognition model, and the psychological and physiological features of the pilot of the aviation accident aircraft are output to be recorded as second features.

In step 104, the second features are determined to be abnormal or not according to the historical psychological and physiological features of the pilot of the aviation accident aircraft and the first features.

In step 105, if the second features are determined to be abnormal, causes of the aviation accident are analyzed for the pilot of the aviation accident aircraft.

In step 106: if the second features are determined to be normal, accident simulation reproduction is performed according to the second features to obtain reproduced accident information.

In step 107, the causes of the aviation accident are analyzed according to the reproduced accident information.

In the present embodiment, obtaining the first EEG signals in Step 101 may specifically include the following steps 1011 to 1014.

In step 1011, the EEG signals of various pilots during training flight in different flight environments are obtained to be recorded as second EEG signals.

In step 1012, the EEG signals of various pilots during actual flight in different flight environments are obtained to be recorded as third EEG signals.

The second EEG signals and the third EEG signals are obtained by a non-invasive method.

In step 1013, the second EEG signals are corrected by using the third EEG signals to obtain corrected EEG signals to be recorded as fourth EEG signals.

In step 1014, the first EEG signals may include the third EEG signals and the fourth EEG signals.

In the present embodiment, the brain-computer aided analysis method for an aviation accident may further include a step of performing signal denoising, artifact removal and feature extraction processing on the first EEG signals.

Specifically, an Faraday cage, threshold method or band-pass filter is used for signal denoising. A linear model analysis method, principal component analysis method or independent component analysis method is used for artifact removal. A frequency domain analysis method or time domain analysis method is used for feature extraction.

The principle of the present disclosure is described in detail below:

I. Data Acquisition

Figure 2:
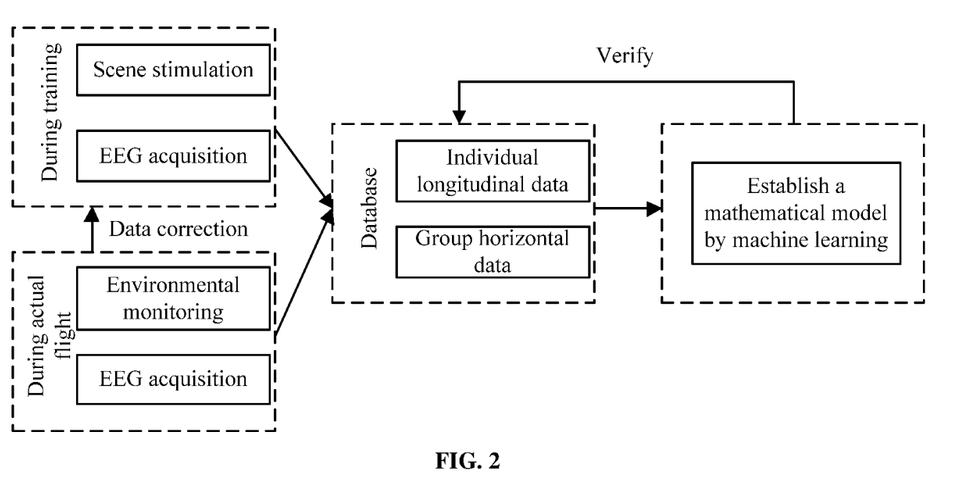
FIG. 2 is a diagram showing a process of establishing a database and a feature recognition model according to Embodiment 1 of the present disclosure.

Data acquisition begins upon pilot training. The simulator generates different flight environments to obtain the EEG signals generated by pilots during training in different states. Due to the difference between the simulator and the real environment and the fact that people are more relaxed during training, it is difficult for the data obtained during training to reflect the real psychological situation. Therefore, it is necessary to use the actual flight data to correct the training data. After data correction, an individual longitudinal database of pilots and a horizontal database of a group of pilots are established. FIG. 2 is a diagram showing a process of establishing a database and a feature recognition model according to Embodiment 1 of the present disclosure.

In addition, it is necessary to monitor: the flight environment, such as the driving environment in the training mode, the driving environment during flight, including flight status parameters, such as flight speed, flight altitude, the current state of all instruments; and external environmental parameters, such as the weather environment outside the cabin. On one hand, the flight environment, one of the external excitation sources of the EEG signals, may affect the psychological activities of the pilots. On the other hand, the flight environment may be fed back to the pilots from a more macroscopic perspective for aiding in flight.

The EEG signals may be obtained by using a non-invasive method. Combined with a brain-computer interface device, electrodes are arranged on driving helmets to obtain the neuronal electrical signals generated by the brain, so as to obtain the original EEG signals.

II. Machine Learning/Deep Learning

Figure 3:
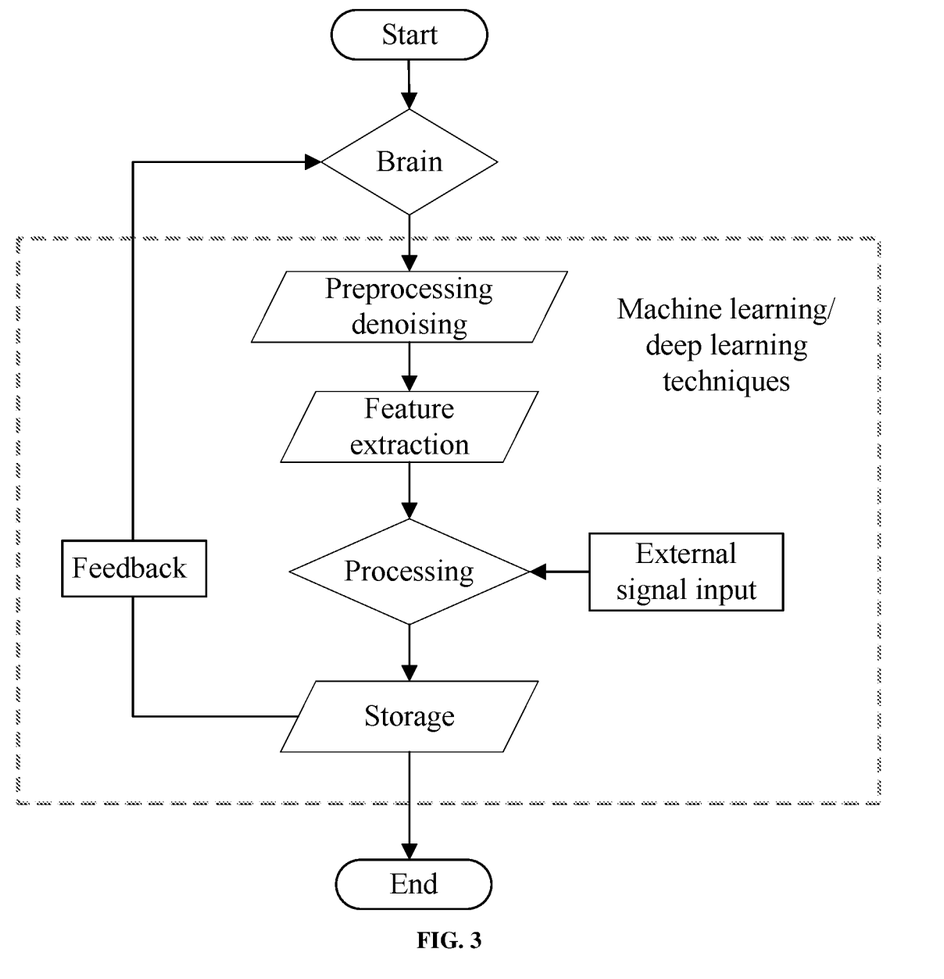
FIG. 3 is a diagram showing a process of preprocessing EEG signals according to Embodiment 1 of the present disclosure.

Firstly, preprocessing is performed on the original EEG signals, including signal denoising, artifact removal and feature extraction. FIG. 3 is a diagram showing a process of preprocessing EEG signals according to Embodiment 1 of the present disclosure.

The signal denoising process includes filtering the external environment and interference generated by the pilot's own body. The external environment may be suppressed by the Faraday cage. A cage made of metal or good conductor is used to prevent electromagnetic fields from entering or escaping. The protection suit for flight may also be specially treated to achieve the same effect. The threshold method may also be used for signal denoising, and data with a signal amplitude exceeding a certain threshold is completely discarded. Alternatively, a band-pass filter may be used for filtering processing, so as to remove noise and motion artifacts within the low-frequency and extremely high-frequency range in the EEG signals. Power frequency noise from the power supply is removed by a notch filter. Through band elimination and notch filtering method, a time domain signal can be converted to a frequency domain signal for being processed by a filter of a certain frequency, and then be switched back to the time domain signal.

The linear model analysis method, principal component analysis method and independent component analysis method and so on may be used for artifact removal.

For feature extraction, back on the characteristic that the frequencies of signals generated from brain activities are different, methods such as Fourier analysis may be used for frequency domain analysis, or a specific model may be established for time domain analysis, so as to extract characteristic signals. Combining techniques based on frequency domain, time domain or wavelet analysis with spatial filtering techniques can achieve dimensionality reduction (principal component analysis (PCA)), separate the source signal from the mixed signal (independent component analysis (ICA)) or increase the distinguishability among different types of output signals (common spatial pattern (CSP), linear model analysis), and then the feature technique can be extracted. After the signal processing is completed, it is stored on the external medium in the black box.

Then a feature recognition model is constructed. The EEG signal is a discrete signal segment. Each signal segment is an EEG signal in a certain time domain. Data are classified according to the types of the analyzed target, such as the sensory, emotional, and physiological features of the pilot. The feature recognition model with signals as input is established, so as to apply to psychological and physiological status recognition of the subject. Among them, one part of the database data is used to establish a mathematical model, and the other part is used to verify the accuracy of the mathematical model. If the model is inaccurate, the model is updated iteratively to obtain a new model.

In addition, the external environment is also a factor affecting the EEG signals of pilots. Combined with the external environment factor, used as an environmental excitation signal in corresponding scene, a data relationship is established. When the aircraft emits an alarm, the flight states is fed back to the pilot, who determines whether the aircraft is in a fault state in combination with the flight environment, flight states and formal data on the instrument panel and trouble light, sensor, etc. When a fault occurs, the information feedback is transmitted to the pilot to assist the pilot to determine the cause of the failure and then perform corresponding manipulation actions, which can avoid the misjudgment of the pilot upon occurrence of the fault and in turn avoid the occurrence of an accident.

III. Aviation Accident Analysis

Figure 4:
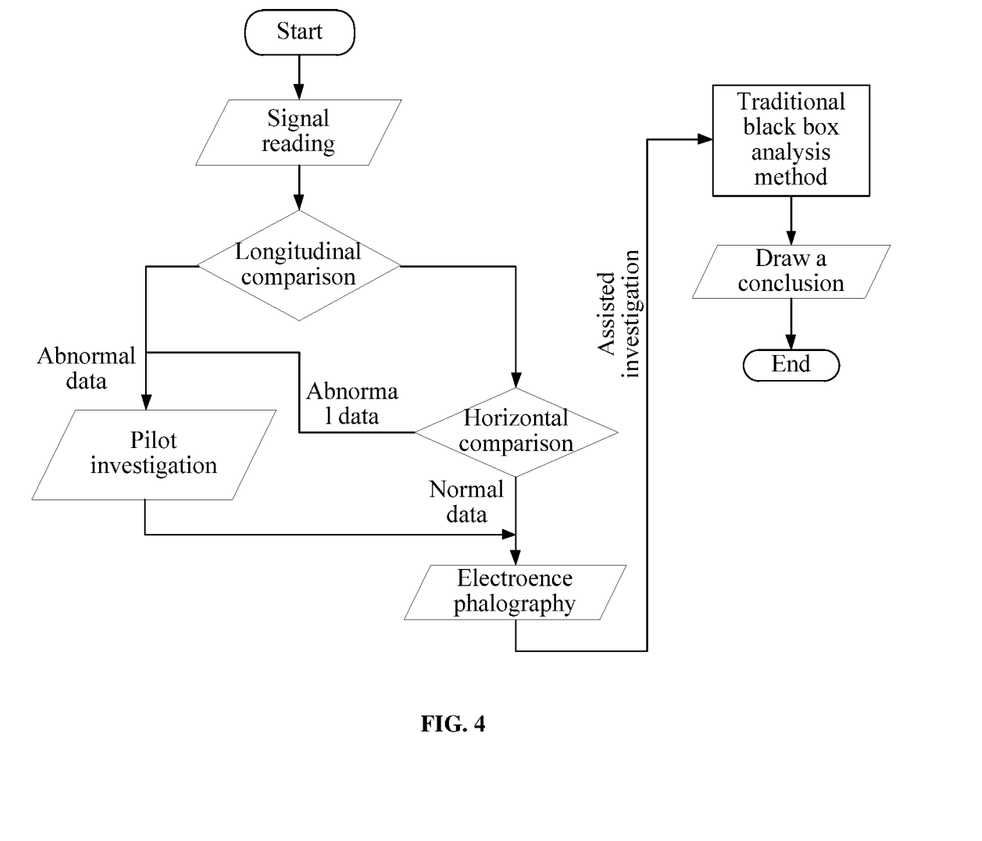
FIG. 4 is a diagram showing a process of aviation accident analysis according to Embodiment 1 of the present disclosure.

FIG. 4 is a diagram showing a process of aviation accident analysis according to Embodiment 1 of the present disclosure. As shown in FIG. 3, during analysis, the EEG signals in the black box is read, and the psychological and physiological features of the pilot is analyzed according to the established feature recognition model and compared with data in the database.

During data comparison, the read EEG signals are firstly compared longitudinally, that is, data matching is performed between the EEG signals and the established individual longitudinal database, so as to determine whether the accident is caused by human factors. If the longitudinal comparison is qualified, the data will be compared horizontally, that is, the data of the pilot will be compared with other samples in the pilot group, and the horizontal comparison will be used to analyze whether the accident is caused by human factors. If the comparison result differs significantly from the known data in similar flight environment in the database, the individual pilot may be investigated and the investigation result may be used as evidence that the accident was caused by human factors.

Part of the bands in the EEG signals may also be used to fuzzily reproduce the scenes that the pilot sees. When the possibility that the accident is caused by personal reasons is eliminated, a specific band in the EEG signals may be used to reproduce the visual image in front of the pilot when the fault occurs, thereby assisting the traditional black box analysis method in reproducing the cockpit environment and the image outside the portholes from the pilot's perspective, building the accident scene and environment, and analyzing the causes of the accident.

The present disclosure records the psychological and physiological features of the pilot during flight, which may be used to confirm or eliminate the cause of the accident from the individual pilot, so as to determine the possibility that the accident is caused by the subjective cause of other personnel. It may also assist the existing method which relies on the black box in analyzing the causes of the accident, and reproduce the accident scene for the identification of the causes of the accident.

Embodiment 2

The present embodiment provides a brain-computer aided analysis system for an aviation accident, including an obtaining module, a training module, a recognition module, a determining module, a first analysis module, a simulation reproduction module, and a second analysis module.

The obtaining module is configured to obtain historical EEG signals and historical psychological and physiological features of various pilots during flight to be recorded as first EEG signals and first features.

The training module is configured to train a feature recognition model by taking the first EEG signals as an input and the first features as an output.

The recognition module is configured to input the EEG signals of the pilot of an aviation accident aircraft into the feature recognition model, and output psychological and physiological features of the pilot of the aviation accident aircraft to be recorded as second features.

The determining module is configured to determine whether the second features are abnormal or not according to the historical psychological and physiological features of the pilot of the aviation accident aircraft and the first features.

The first analysis module is configured to analyze causes of the aviation accident for the pilot of the aviation accident aircraft if the second features are abnormal.

The simulation reproduction module is configured to perform accident simulation reproduction according to the second features to obtain reproduced accident information if the second features are not abnormal.

The second analysis module is configured to analyze the causes of the aviation accident according to the reproduced accident information.

In the present embodiment, the obtaining module may specifically include a first obtaining unit, a second obtaining unit, and a correction unit.

The first obtaining unit is configured to obtain the EEG signals of various pilots during training flight in different flight environments, to be recorded as second EEG signals.

The second obtaining unit is configured to obtain the EEG signals of various pilots during actual flight in different flight environments, to be recorded as third EEG signals.

The correction unit is configured to correct the second EEG signals by using the third EEG signals to obtain corrected EEG signals, to be recorded as fourth EEG signals.

The first EEG signals may include the third EEG signals and the fourth EEG signals.

Further, the second EEG signals and the third EEG signals are obtained by a non-invasive method.

In the present embodiment, the brain-computer aided analysis system for an aviation accident may further include a processing module, a signal denoising unit, an artifact removal unit, and a feature extraction unit.

The processing module is configured to perform signal denoising, artifact removal and feature extraction processing on the first EEG signals. Further, the processing module may specifically include a signal denoising unit, an artifact removal unit and a feature extraction unit.

The signal denoising unit is configured to use an Faraday cage, a threshold method or a band-pass filter for signal denoising.

The artifact removal unit is configured to use a linear model analysis method, a principal component analysis method or an independent component analysis method for artifact removal.

The feature extraction unit is configured to use a frequency domain analysis method or a time domain analysis method for feature extraction.

Each embodiment of the present specification is described in a progressive manner, each embodiment focuses on the difference from other embodiments, and the same and similar parts between the embodiments may refer to each other. Since the system disclosed in the embodiments corresponds to the method disclosed in the embodiments, the description is relatively simple, and reference can be made to the method description.

In this specification, several specific embodiments are used for illustration of the principles and implementations of the present disclosure. The description of the foregoing embodiments is used to help illustrate the method of the present disclosure and the core ideas thereof. In addition, those of ordinary skill in the art can make various modifications in terms of specific implementations and the scope of application in accordance with the ideas of the present disclosure. In conclusion, the content of this specification shall not be construed as a limitation to the present disclosure

What is claimed is:

1. A brain-computer aided analysis method for an aviation accident, comprising:
    obtaining historical electroencephalogram (EEG) signals and historical psychological and physiological features of various pilots during flight to be recorded as first EEG signals and first features;
    training a feature recognition model by using the first EEG signals as an input and the first features as an output;
    inputting EEG signals of a pilot of an aviation accident aircraft into the feature recognition model, and outputting psychological and physiological features of the pilot of the aviation accident aircraft to be recorded as second features;
    determining whether the second features are abnormal or not according to the historical psychological and physiological features of the pilot of the aviation accident aircraft and the first features; and
    if the second features is determined to be abnormal, analyzing causes of the aviation accident for the pilot of the aviation accident aircraft; or
    if the second features is determined to be not abnormal, performing accident simulation reproduction according to the second features to obtain reproduced accident information; and
    analyzing the causes of the aviation accident according to the reproduced accident information.

2. The brain-computer aided analysis method for the aviation accident according to claim 1, wherein obtaining the first EEG signals comprises:
    obtaining the EEG signals of the various pilots during training flight in different flight environments to be recorded as second EEG signals;
    obtaining the EEG signals of the various pilots during actual flight in different flight environments to be recorded as third EEG signals; and
    correcting the second EEG signals by using the third EEG signals to obtain corrected EEG signals to be recorded as fourth EEG signals,
    wherein the first EEG signals comprise the third EEG signals and the fourth EEG signals.

3. The brain-computer aided analysis method for the aviation accident according to claim 2, wherein the second EEG signals and the third EEG signals are obtained by a non-invasive method.

4. The brain-computer aided analysis method for the aviation accident according to claim 1, further comprising:
    performing signal denoising, artifact removal and feature extraction processing on the first EEG signals.

5. The brain-computer aided analysis method for the aviation accident according to claim 4, wherein the performing signal denoising, artifact removal and feature extraction processing on the first EEG signals comprises:
    using an Faraday cage, a threshold method or a band-pass filter for signal denoising;
    using a linear model analysis method, a principal component analysis method or an independent component analysis method for artifact removal; and
    using a frequency domain analysis method or a time domain analysis method for feature extraction.

6. A brain-computer aided analysis system for an aviation accident, comprising:
    an obtaining module, configured to obtain historical EEG signals and historical psychological and physiological features of various pilots during flight to be recorded as first EEG signals and first features;
    a training module, configured to train a feature recognition model by using the first EEG signals as an input and the first features as an output;
    a recognition module, configured to input EEG signals of a pilot of an aviation accident aircraft into the feature recognition model, and output psychological and physiological features of the pilot of the aviation accident aircraft to be recorded as second features;
    a determining module, configured to determine whether the second features are abnormal or not according to the historical psychological and physiological features of the pilot of the aviation accident aircraft and the first features;
    a first analysis module, configured to analyze causes of the aviation accident for the pilot of the aviation accident aircraft if the second features are abnormal;
    a simulation reproduction module, configured to perform accident simulation reproduction according to the second features to obtain reproduced accident information if the second features are not abnormal; and a second analysis module, configured to analyze the causes of the aviation accident according to the reproduced accident information.

7. The brain-computer aided analysis system for the aviation accident according to claim 6, wherein the obtaining module comprises:
   a first obtaining unit, configured to obtain the EEG signals of the various pilots during training flight in different flight environments to be recorded as second EEG signals;
   a second obtaining unit, configured to obtain the EEG signals of the various pilots during actual flight in different flight environments to be recorded as third EEG signals; and
   a correction unit, configured to correct the second EEG signals by using the third EEG signals to obtain corrected EEG signals to be recorded as fourth EEG signals.

8. The brain-computer aided analysis system for the aviation accident according to claim 7, wherein the second EEG signals and the third EEG signals are obtained by a non-invasive method.

9. The brain-computer aided analysis system for the aviation accident according to claim 6, further comprising:
   a processing module, configured to perform signal denoising, artifact removal and feature extraction processing on the first EEG signals.

10. The brain-computer aided analysis system for the aviation accident according to claim 9, wherein the processing module comprises:
   a signal denoising unit, configured to use an Faraday cage, a threshold method or a band-pass filter for signal denoising;
   an artifact removal unit, configured to use a linear model analysis method, a principal component analysis method or an independent component analysis method for artifact removal; and
   a feature extraction unit, configured to use a frequency domain analysis method or a time domain analysis method for feature extraction.

* * * * *